United States Patent
Hadley-Fruit

(10) Patent No.: US 6,524,288 B1
(45) Date of Patent: Feb. 25, 2003

(54) DRAINAGE RESERVOIR SUPPORT ASSEMBLY

(76) Inventor: Michelle Hadley-Fruit, 1912 E. Alder Ave., Walla Walla, WA (US) 99362

( * ) Notice: Subject to any disclaimer, the term of this patent is extended or adjusted under 35 U.S.C. 154(b) by 0 days.

(21) Appl. No.: 09/939,027

(22) Filed: Aug. 24, 2001

(51) Int. Cl.[7] .............................. A61M 1/00; A45F 3/02
(52) U.S. Cl. ...................... 604/322; 604/317; 604/345; 604/353; 224/607; 224/623
(58) Field of Search ................... 604/541, 543, 604/317, 322, 331, 345, 353; 224/607, 610, 612, 625, 626, 623; 220/903

(56) References Cited

U.S. PATENT DOCUMENTS

| | | | |
|---|---|---|---|
| 1,470,334 A | * 10/1923 | Stensgaard et al. | |
| 2,896,624 A | 7/1959 | Candido | |
| 2,943,660 A | * 7/1960 | Seeger | |
| 3,733,008 A | * 5/1973 | Churchill et al. | |
| 3,856,011 A | 12/1974 | Blanchard | |
| 3,997,092 A | * 12/1976 | Pogwizd | |
| 4,086,925 A | 5/1978 | Dodge | |
| 4,176,773 A | * 12/1979 | Wilkinson | |
| 4,248,366 A | * 2/1981 | Christiansen | |
| 4,256,110 A | 3/1981 | Scoville | |
| D261,077 S | 10/1981 | Loomis | |
| 4,733,807 A | * 3/1988 | Porter et al. | |
| D304,890 S | * 12/1989 | Cannan | |
| 4,892,527 A | * 1/1990 | Zivny | |
| 4,901,375 A | * 2/1990 | Dahlgren | |
| 4,974,761 A | * 12/1990 | Luque | |
| D340,583 S | * 10/1993 | Kahn | |
| D353,520 S | * 12/1994 | Schwartz | |
| 5,398,855 A | * 3/1995 | Schaiewitz | |
| 5,429,623 A | * 7/1995 | Dessel | |
| 5,454,497 A | * 10/1995 | Kettelson | |
| 5,643,233 A | * 7/1997 | Turner | |
| 5,687,896 A | 11/1997 | Clift | |
| 5,864,289 A | * 1/1999 | Tiemann | |
| 6,152,915 A | * 11/2000 | Watson et al. | |

\* cited by examiner

*Primary Examiner*—Dennis Ruhl

(57) ABSTRACT

A drainage reservoir support assembly for supporting a reservoir of a medical drainage device inserted in a body of a user. The drainage reservoir support assembly includes at least one container for containing the reservoir of a medical drainage device. A first end of the container includes an access opening for providing access to an interior of the container. In one embodiment of the present invention, the reservoir of the medical drainage device is removably insertable in the interior of the container. A strap is provided for removably supporting the container from the neck of a user. The strap includes a first end and a second end with each of the ends of the strap being mounted on a peripheral wall of the container such that the strap forms a loop.

19 Claims, 3 Drawing Sheets

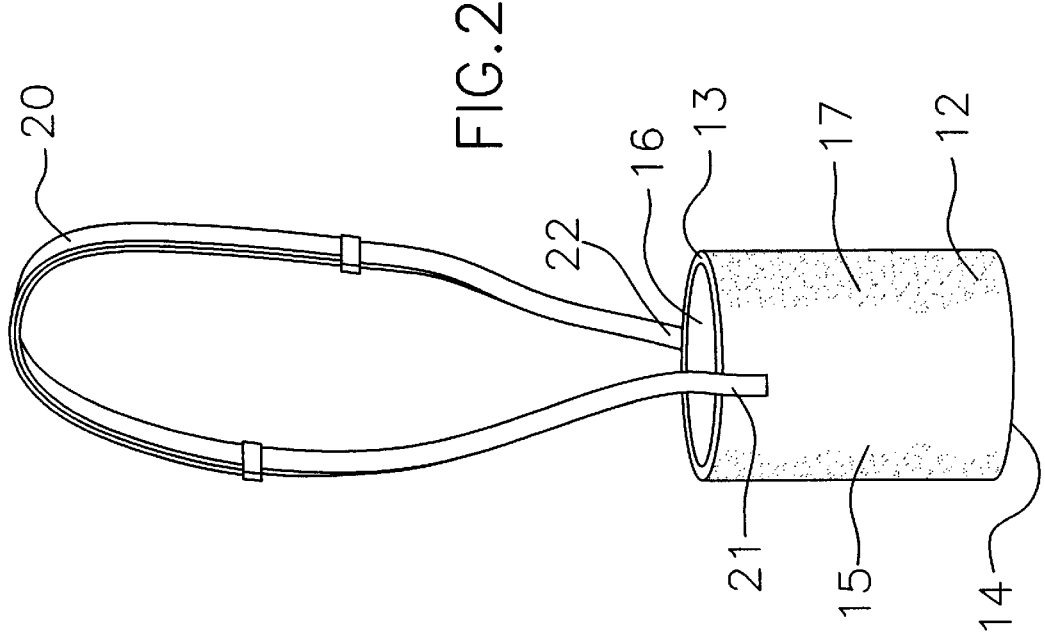
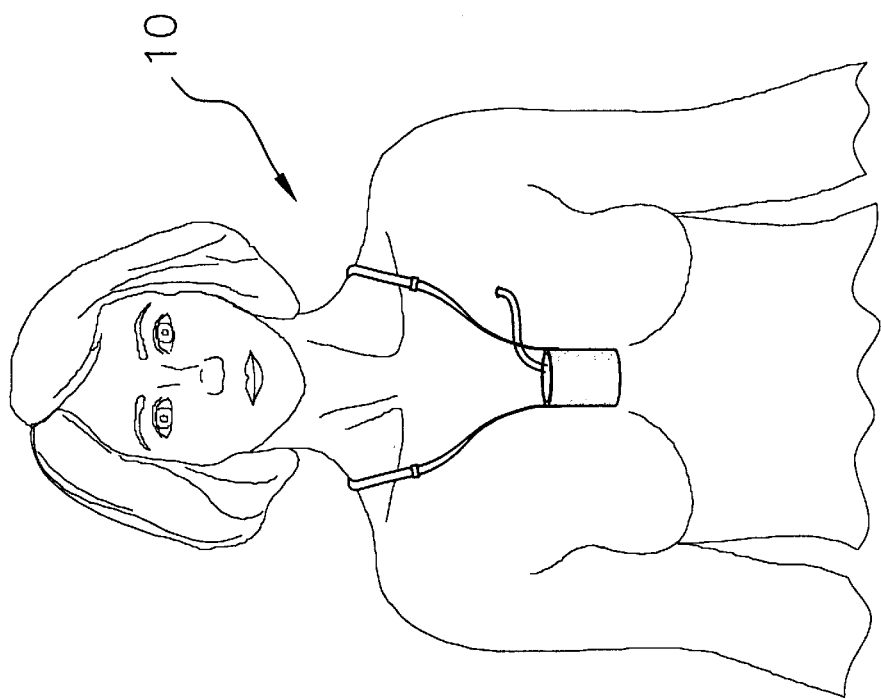

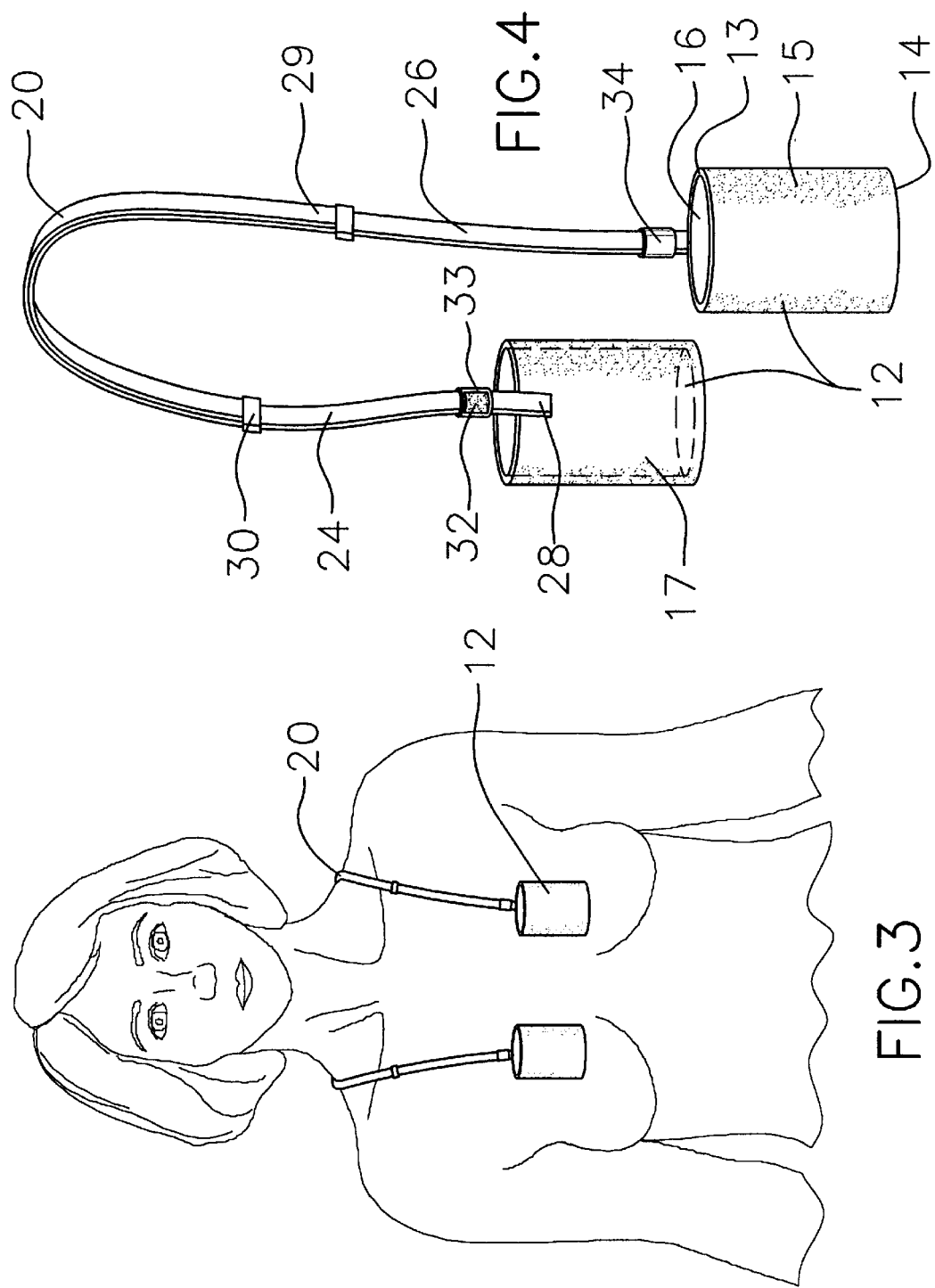

DRAINAGE RESERVOIR SUPPORT ASSEMBLY

BACKGROUND OF THE INVENTION

1. Field of the Invention

The present invention relates to medical supporting devices and more particularly pertains to a new drainage reservoir support assembly for supporting a reservoir of a medical drainage device from a neck of a user.

2. Description of the Prior Art

The use of medical supporting devices is known in the prior art. More specifically, medical supporting devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 3,856,011; 5,687,896; 4,086,925; 4,256,110; 2,896,624; and U.S. Pat. No. Des. 361,077.

While these devices fulfill their respective, particular objectives and requirements, the aforementioned patents do not disclose a new drainage reservoir support assembly. The inventive device includes at least one container for containing the reservoir of a medical drainage device. A first end of the container includes an access opening for providing access to an interior of the container. In one embodiment of the present invention, the reservoir of the medical drainage device is removably insertable in the interior of the container. A strap is provided for removably supporting the container from the neck of a user. The strap includes a first end and a second end with each of the ends of the strap being mounted on a peripheral wall of the container such that the strap forms a loop.

In these respects, the drainage reservoir support assembly according to the present invention substantially departs from the conventional concepts and designs of the prior art, and in so doing provides an apparatus primarily developed for the purpose of supporting a reservoir of a medical drainage device inserted in a body of a user from a neck of a user.

SUMMARY OF THE INVENTION

In view of the foregoing disadvantages inherent in the known types of medical supporting devices now present in the prior art, the present invention provides a new drainage reservoir support assembly construction wherein the same can be utilized for supporting a reservoir of a medical drainage device inserted in a body of a user from a neck of a user.

The general purpose of the present invention, which will be described subsequently in greater detail, is to provide a new drainage reservoir support assembly apparatus and method which has many of the advantages of the medical supporting devices mentioned heretofore and many novel features that result in a new drainage reservoir support assembly which is not anticipated, rendered obvious, suggested, or even implied by any of the prior art medical supporting devices, either alone or in any combination thereof.

To attain this, the present invention generally comprises at least one container for containing the reservoir of a medical drainage device. A first end of the container includes an access opening for providing access to an interior of the container. In one embodiment of the present invention, the reservoir of the medical drainage device is removably insertable in the interior of the container. A strap is provided for removably supporting the container from the neck of a user. The strap includes a first end and a second end with each of the ends of the strap being mounted on a peripheral wall of the container such that the strap forms a loop.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new drainage reservoir support assembly apparatus and method which has many of the advantages of the medical supporting devices mentioned heretofore and many novel features that result in a new drainage reservoir support assembly which is not anticipated, rendered obvious, suggested, or even implied by any of the prior art medical supporting devices, either alone or in any combination thereof.

It is another object of the present invention to provide a new drainage reservoir support assembly which may be easily and efficiently manufactured and marketed.

It is a further object of the present invention to provide a new drainage reservoir support assembly which is of a durable and reliable construction.

An even further object of the present invention is to provide a new drainage reservoir support assembly which is susceptible of a low cost of manufacture with regard to both materials and labor, and which accordingly is then susceptible of low prices of sale to the consuming public, thereby making such drainage reservoir support assembly economically available to the buying public.

Still yet another object of the present invention is to provide a new drainage reservoir support assembly which provides in the apparatuses and methods of the prior art some of the advantages thereof, while simultaneously overcoming some of the disadvantages normally associated therewith.

Still another object of the present invention is to provide a new drainage reservoir support assembly for supporting a reservoir of a medical drainage device inserted in a body of a user from a neck of a user.

Yet another object of the present invention is to provide a new drainage reservoir support assembly which includes at least one container for containing the reservoir of a medical drainage device. A first end of the container includes an access opening for providing access to an interior of the container. In one embodiment of the present invention, the reservoir of the medical drainage device is removably insertable in the interior of the container. A strap is provided for removably supporting the container from the neck of a user. The strap includes a first end and a second end with each of the ends of the strap being mounted on a peripheral wall of the container such that the strap forms a loop.

Still yet another object of the present invention is to provide a new drainage reservoir support assembly that supports the reservoir of the medical drainage device from the neck of the user instead of attaching the reservoir to the hospital garment of the user. Prior to the present invention a reservoir attached to the hospital garment of the had a tendency to pull the hospital garment in an anterior direction with respect to the user causing the rear of the user to be exposed. The present invention supports the reservoir from the neck of the user eliminating the need of attaching the reservoir to a hospital garment.

Even still another object of the present invention is to provide a new drainage reservoir support assembly that reduces the amount of pain experienced by a user having a reservoir attached to a hospital garment. Since a reservoir attached to a hospital garment has a tendency to move as the user moves, the reservoir may pull on an attached drain tube that enters the body of the user causing pain. The present invention supports the reservoir from the neck of the user keeping it close the body of the user and preventing it from pulling on the drain tube.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new drainage reservoir support assembly according to the present invention.

FIG. 2 is a schematic perspective view of the present invention illustrating a single container.

FIG. 3 is a schematic perspective view of an alternate embodiment of the present invention illustrating a pair of containers being employed.

FIG. 4 is a schematic perspective view of the present invention.

DESCRIPTION OF THE PREFERRED EMBODIMENT

Figure 5:
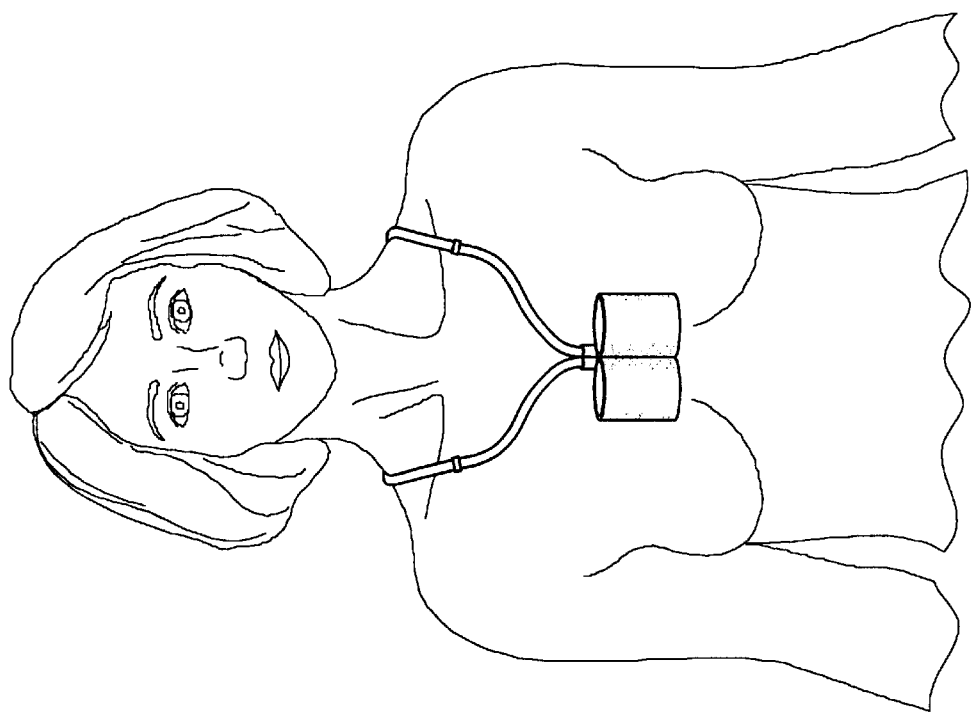
FIG. 5 is a schematic perspective view of the present invention.

With reference now to the drawings, and in particular to FIGS. 1 through 5 thereof, a new drainage reservoir support assembly embodying the principles and concepts of the present invention and generally designated by the reference numeral 10 will be described.

As best illustrated in FIGS. 1 through 5, the drainage reservoir support assembly 10 generally comprises at least one container 12 for containing the reservoir of a medical drainage device such as, for example, a Jackson-Pratt surgical drainage device. The at least one container 12 includes a first end 13, a second end 14, a peripheral wall 15 extending between the first 13 and second 14 ends of the container 12. The container 12 includes a longitudinal axis that extends between the first 13 and second 14 ends of the container 12.

The first end 13 of the container 12 preferably includes an access opening 16 for providing access to an interior 17 of the container 12. In one embodiment of the present invention, the reservoir of the medical drainage device is removably insertable in the interior 17 of the container 12. The container 12 may hold a variety of reservoirs with varying volumes such as, for example, from 100 cubic centimeters to 400 cubic centimeters. However, it is possible to employ containers 12 capable of supporting reservoirs having a volume less than 100 cubic centimeters and greater than 400 cubic centimeters.

The container 12 may be generally cylindrical such that the container 12 includes a generally circular transverse cross section taken substantially perpendicular to the longitudinal axis of the container 12. Additionally, the container 12 may comprise a substantially rigid material such as, for example, a plastic or steel material.

A strap 20 is provided for removably supporting the container 12 from the neck of a user. The strap 20 includes a first end 21 and a second end 22. Each of the ends 21 and 22 of the strap 20 are mounted on the peripheral wall 15 of the container 12 such that the strap 20 forms a loop. The ends 21 and 22 of the strap 20 may be diametrically opposed to each other with respect to the access opening 16 of the container 12. In one embodiment of the present invention, the container 12 is positionable in an anterior position with respect to the body of the user.

In an alternate embodiment of the present invention, as particularly illustrated in FIGS. 2, 3 and 4, a pair of the containers 12 is employed. The strap 20 is coupled to and extends between each of the containers 12. The first end 21 of the strap 20 is mounted on the peripheral wall 15 of one of the containers 12 and the second end 22 of the strap 20 is mounted on the peripheral wall 15 of the other container 12.

In either embodiment of the present invention, the strap 20 may include a first strap portion 24 and a second strap portion 26 adjustable coupled together. The first 24 and second 26 strap portions permit the container 12 or containers 12 to be adjustably positioned with respect to a longitudinal axis of the body of the user. Each of the strap portions 24 and 26 includes a first end 28 and a second end 29.

In one embodiment of the present invention, the first end 28 of each of the strap portions 24 and 26 may be mounted on the peripheral wall 15 of the containers 12. The second end 29 of each of the strap portions 24 and 26 may include an annular loop 30 formed thereon with a portion of the first strap portion 24 being slidably positioned through the annular loop 30 formed on the second strap portion 26 and a portion of the second strap portion 26 being slidably positioned through the annular loop 30 formed on the second end 29 of the first strap portion 24. A length of the strap 20 is adjustable by pulling on each of the first ends 28 of each of the strap portions 24 and 26.

As particularly illustrated in FIG. 4, a coupling member 32 may be provided for releaseably coupling the first 21 and second 22 ends of the strap 20 together. The coupling member 32 may include a first coupling portion 33 and a second coupling portion 34. The first coupling portion 33 may be mounted on a portion of the strap 20 positioned generally adjacent to the first end 21 of the strap 20. The second coupling portion 34 may be mounted on a portion of the strap 20 positioned generally adjacent to the second end 22 of the strap 20. As particularly illustrated in FIG. 5, In an embodiment of the present invention employing more than one container 12, the first 33 and second 34 coupling portions are releaseably couplable such that each of the containers 12 are positioned generally adjacent to each other when the first and second coupling portions are coupled together. The coupling member 32 may comprise a hook and loop fastener.

In use, the container 12 is supported from the neck of a user. Depending upon the location on the body of the user the drainage device is used, the length of the strap 20 may be lengthened or shortened to position the container 12 closest to the drainage device. The reservoir of the drainage device is then inserted into the interior 17 of the container 12 through the access opening 16.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A drainage reservoir support assembly for supporting a reservoir of a medical drainage device inserted in a body of a user, said support assembly being supported about a neck of a user, said assembly comprising:
   a pair of containers for containing the reservoir of the medical drainage device, a first end of each of said containers having an access opening for providing access to an interior of said container, wherein the reservoir of the medical drainage device is removably insertable in the interior of each of said containers;
   a strap for removably supporting said containers from the neck of a user, said strap having a first end and a second end, each of said ends of said strap being mounted on a peripheral wall of one of said containers such that said strap forms a loop, wherein said containers are positionable adjacent to the body of the user.

2. The drainage reservoir support assembly of claim 1, wherein each of said containers is generally cylindrical such that said at least one container having a generally circular transverse cross section taken substantially perpendicular to a longitudinal axis of said at least one container.

3. The drainage reservoir support assembly of claim 1, wherein each of said containers comprises a substantially rigid material.

4. The drainage reservoir support assembly of claim 1, wherein said strap has a first strap portion and a second strap portion adjustably coupled together, each of said strap portions having a first end and a second end.

5. A drainage reservoir support assembly for supporting a reservoir of a medical drainage device inserted in a body of a user, said support assembly being supported about a neck of a user, said assembly comprising:
   at least one container for containing the reservoir of the medical drainage device, a first end of said at least one container having an access opening for providing access to an interior of said at least one container, wherein the reservoir of the medical drainage device is removably insertable in the interior of said at least one container;
   a strap for removably supporting said at least one container from the neck of a user, said strap having a first end and a second end, each of said ends of said strap being mounted on a peripheral wall of said at least one container such that said strap forms a loop, wherein said at least one container is positionable adjacent to the body of the user;
   wherein said strap has a first strap portion and a second strap portion adjustably coupled together, each of said strap portions having a first end and a second end; and
   wherein said first end of each of said strap portions is mounted on a peripheral wall of said at least one container; wherein said second end of each of said strap portions has an annular loop formed thereon, a portion of said first strap portion being slidably positioned through said annular loop formed on said second strap portion, a portion of said second strap portion being slidably positioned through said annular loop formed on said second end of said first strap portion, wherein a length of said strap is adjustable by pulling said first ends of said first and second strap portions away from each other.

6. A drainage reservoir support assembly for supporting a reservoir of a medical drainage device inserted in a body of a user, said support assembly being supported about a neck of a user, said assembly comprising:
   at least one container for containing the reservoir of the medical drainage device, a first end of said at least one container having an access opening for providing access to an interior of said at least one container, wherein the reservoir of the medical drainage device is removably insertable in the interior of said at least one container;
   a strap for removably supporting said at least one container from the neck of a user, said strap having a first end and a second end, each of said ends of said strap being mounted on a peripheral wall of said at least one container such that said strap forms a loop, wherein said at least one container is positionable adjacent to the body of the user; and a coupling member mounted on said strap for releasably coupling said first and second ends of said strap together.

7. The drainage reservoir support assembly of claim 1, wherein said coupling member has a first coupling portion and a second coupling portion, said first coupling portion being mounted on a portion of said strap positioned generally adjacent to said first end of said strap, said second coupling portion being mounted on a portion of said strap positioned generally adjacent to said second end of said strap, said first and second coupling portions being releasably couplable.

8. The drainage reservoir support assembly of claim 1, wherein said coupling member comprises a hook and loop fastener.

9. The drainage reservoir support assembly of claim 5, wherein said at least one container being generally cylindrical such that said at least one container having a generally circular transverse cross section taken substantially perpendicular to a longitudinal axis of said at least one container.

10. The drainage reservoir support assembly of claim 5, wherein said at least one container comprises a substantially rigid material.

11. The drainage reservoir support assembly of claim 5, wherein said at least one container comprises a pair of containers, each end of said strap being mounted on a peripheral wall of each of said pair of containers.

12. The drainage reservoir support assembly of claim 5, additionally including a coupling member mounted on said strap for releasably coupling said first and second ends of said strap together.

13. The drainage reservoir support assembly of claim 12, wherein said coupling member has a first coupling portion and a second coupling portion, said first coupling portion being mounted on a portion of said strap positioned generally adjacent to said first end of said strap, said second coupling portion being mounted on a portion of said strap positioned generally adjacent to said second end of said strap, said first and second coupling portions being releasably couplable.

14. The drainage reservoir support assembly of claim 12, wherein said coupling member comprises a hook and loop fastener.

15. The drainage reservoir support assembly of claim 6, wherein said coupling member has a first coupling portion and a second coupling portion, said first coupling portion being mounted on a portion of said strap positioned generally adjacent to said first end of said strap, said second coupling portion being mounted on a portion of said strap positioned generally adjacent to said second end of said strap, said first and second coupling portions being releasably couplable.

16. The drainage reservoir support assembly of claim 6, wherein said coupling member comprises a book and loop fastener.

17. The drainage reservoir support assembly of claim 6, wherein said at least one container being generally cylindrical such that said at least one container having a generally circular transverse cross section taken substantially perpendicular to a longitudinal axis of said at least one container.

18. The drainage reservoir support assembly of claim 6, wherein said at least one container comprises a substantially rigid material.

19. The drainage reservoir support assembly of claim 6, wherein said strap has a first strap portion and a second strap portion adjustably coupled together, each of said strap portions having a first end and a second end.

* * * * *